United States Patent
Hillenbrand et al.

(10) Patent No.: US 7,606,612 B2
(45) Date of Patent: Oct. 20, 2009

(54) SYSTEM AND METHOD TO PERFORM PARALLEL IMAGING

(75) Inventors: Claudia M. Hillenbrand, Cordova, TN (US); Mark A. Griswold, Shaker Hts, OH (US); Eddy Wong, Richmond Heights, OH (US); Jeffrey Duerk, Avon Lake, OH (US)

(73) Assignee: Case Western Reserve University, Cleveland, OH (US)

( * ) Notice: Subject to any disclaimer, the term of this patent is extended or adjusted under 35 U.S.C. 154(b) by 267 days.

(21) Appl. No.: 11/132,989

(22) Filed: May 19, 2005

(65) Prior Publication Data

US 2006/0293586 A1    Dec. 28, 2006

(51) Int. Cl.
*A61B 5/055* (2006.01)
*G01V 3/00* (2006.01)

(52) U.S. Cl. .................... 600/423; 600/410; 600/422; 324/318

(58) Field of Classification Search .......... 600/410, 600/423; 324/307, 309, 318
See application file for complete search history.

(56) References Cited

U.S. PATENT DOCUMENTS

| | | | |
|---|---|---|---|
| 6,083,167 A * | 7/2000 | Fox et al. ............... 600/439 |
| 6,289,232 B1 | 9/2001 | Jakob et al. |
| 6,380,740 B1 * | 4/2002 | Laub ................ 324/309 |
| 6,545,472 B2 | 4/2003 | Prüssmann et al. |
| 6,734,673 B2 | 5/2004 | Agrikola |
| 6,828,788 B2 | 12/2004 | Wang |
| 6,828,791 B2 * | 12/2004 | Morita et al. .......... 324/318 |
| 6,841,998 B1 | 1/2005 | Griswold |
| 6,853,190 B2 | 2/2005 | Nittka et al. |
| 6,961,608 B2 * | 11/2005 | Hoshino et al. ........ 600/423 |
| 6,980,001 B2 * | 12/2005 | Paley et al. ........... 324/318 |
| 7,218,108 B2 * | 5/2007 | Ichinose et al. ........ 324/309 |
| 2004/0044280 A1 * | 3/2004 | Paley et al. ........... 600/410 |
| 2004/0222794 A1 | 11/2004 | Griswold et al. |
| 2005/0054913 A1 | 3/2005 | Duerk et al. |
| 2005/0054914 A1 | 3/2005 | Duerk et al. |
| 2006/0074295 A1 * | 4/2006 | Kucharczyk et al. ... 600/422 |

OTHER PUBLICATIONS

Albert C. Lardo, Ph.D., "Real-Time Magnetic Resonance Imaging: Diagnostic and Intervantional Applications," Pediatric Cardiology, Springer-Verlag New York Inc., pp. 80-98, (2000).

(Continued)

*Primary Examiner*—Eric F Winakur
*Assistant Examiner*—Michael T Rozanski

(57) ABSTRACT

A system and method to perform parallel MR imaging are disclosed. The system comprises an MR imaging machine and a probe having at least two MR RF reception coils. Each coil of the probe is operationally connected to a separate receiver channel of the MR imaging machine. The MR imaging machine implements a partially parallel acquisition method to excite precessing nuclear spins, in and around an internal segment of a patient into which the probe is inserted, and to use the coils of the catheter to simultaneously sample a plurality of response signals to form reduced k-space data sets for each of the coils. The plurality of response signals represent nuclear magnetic resonance signals arising from the precessing nuclear spins. The reduced k-space data sets are further processed by the MR imaging machine to generate a full volume dataset of a region in and around the vessel.

15 Claims, 7 Drawing Sheets

OTHER PUBLICATIONS

Jianmin Hua, GC Hurst, JL Duerk, TJ Ryan, AM Cohen, "Intravascular (Catheter) NMR Receiver Coil: Technical Developments and In-Vivo Imaging Results," Works in Progress, Society of Magnetic Resonance in Medicine, Ninth Annual Scientific Meeting and Exhibition, p. 1335, (Aug. 18, 1990).

Jean-Michel Serfaty, Xiaoming Yang, Ananda Kumar, Ergin Atalar, "Coronary Artery Intervention Guided with Magnetic Resonance Imaging," Proc. Intl. Soc. Mag. Reson. Med 9, p. 541, (2001).

Mark E. Ladd, Jörg F. Debatin, "Interventional and Intravascular MR Angiography," Herz Urban & Vogel, Zentrallnstitut für Röntgendiagnostik, Universitätsklinikum Essen (Germany), p. 440-451, (2000).

Walter J. Rogers, Jeffrey W. Prichard, Yong-Lin Hu, Peter R. Olson, Daniel H. Benckart, Christopher M. Kramer, Diane A. Vido, Nathaniel Reichek, "Characterization of Signal Properties in Atherosclerotic Plaque Components by Intravascular MRI," Arterioscler Thromb Vasc Biol., p. 1824-1830, (2000).

Pedro A. Rivas, Krishna S. Nayak, Greig C. Scott, Michael V. McConnell, Adam B. Kerr, Dwight G. Nishimura, John M. Purdy, Bob S. Hu, "In Vivo Real-Time Intravascular MRI," Journal of Cardiovascular Magnetic Resonance, Marcel Dekkar, Inc., 4(2), pp. 223-232, (2002).

O. Dietrich, K. Nikolaou, B.J. Wintersperger, W. Fatz, M. Nittka, R. Petsch, B. Kiefer, S. O. Schoenberg, "iPAT: Applications for Fast and Cardiovascular MR Imaging," electromedia 70, pp. 133-146, (2002).

Mark A. Griswold, Peter M. Jakob, Mathias Nittka, James W. Goldfarb, Axel Haase, "Partially Parallel Imaging With Localized Sensitivities (PILS)," Magnetic Resonance in Medicine, Wiley-Liss, Inc., pp. 602-609, (2000).

Mark A. Griswold, Peter M. Jakob, Robin M. Heidermann, Mathias Nittka, Vladimir Jellus, Jianmin Wang, Berthold Kiefer, Axel Haase, "Generalized Autocalibrating Partially Parallel Acquisitions (GRAPPA)," Magnetic Resonance in Medicine, Wiley-Liss, Inc., pp. 1202-1210, (2002).

C. M. Hillenbrand, D. R. Elgort, E. Y. Wong, A. Reykowski, F. k. Wacker, J. S. Lewin, J. L. Duerk," Active Device Tracking and High-Resolution Intravascular MRI Using a Novel Catheter-Based, Opposed-Solenoid Phased Array Coil," Magnetic Resonance in Medicine, Wiley-Liss, Inc., pp. 668-675, (2004).

* cited by examiner

SYSTEM AND METHOD TO PERFORM PARALLEL IMAGING

TECHNICAL FIELD

Certain embodiments of the present invention relate to magnetic resonance imaging. More particularly, certain embodiments of the present invention relate to a system and method to perform parallel imaging such as, for example, intravascular, three-dimensional (3-D) parallel imaging.

CROSS-REFERENCE TO RELATED APPLICATIONS/INCORPORATION BY REFERENCE

U.S. Pat. No. 6,841,998 issued to Griswold on Jan. 11, 2005 is incorporated by reference herein in its entirety. U.S. Pat. No. 6,853,190 issued to Nittka et al. on Feb. 8, 2005 is incorporated by reference herein in its entirety. U.S. Pat. No. 6,828,788 issued to Wang on Dec. 7, 2004 is incorporated by reference herein in its entirety. U.S. Pat. No. 6,734,673 issued to Agrikola on May 11, 2004 is incorporated by reference herein in its entirety. U.S. Pat. No. 6,289,232 issued to Jakob et al. on Sep. 11, 2001 is incorporated by reference herein in its entirety. Published patent application US 2005/0054914 to Duerk et al. published on Mar. 10, 2005 is incorporated by reference herein in its entirety.

BACKGROUND OF THE INVENTION

Intravascular Ultrasound (IVUS) has recently made inroads on the 3-D assessment of vessel wall anatomy. 3D reconstructions of the entire vessel segment can be performed from cross-sectional IVUS images. Such images help the physician to identify locations of pathology, as well as to evaluate the progression or regression of atherosclerotic disease. Typical IVUS scan specifications include a frame rate of 30 frames per second, a pullback speed of 0.5 mm per second, an in-plane resolution of 50-150 µm, and a slice resolution of about 0.5 to 1.0 mm. The real-time capabilities and the relative ease of use have made IVUS the method of choice for intravascular vessel characterization. However, IVUS is based on acoustic impedance and can, therefore, not offer the variety of contrast mechanisms available with MR. In many ways, MR image quality already seems superior to IVUS and the achievable in-plane resolution is almost comparable. However, to date, intravascular MRI has lagged behind IVUS in imaging speed.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention provides a method to perform parallel MR imaging. The method comprises inserting a probe internally into an organism (e.g., into a blood vessel of a human patient) at a first position. The probe may be, for example, an intravascular catheter and includes at least two MR RF reception coils. Each of the reception coils is operationally connected to a separate receiver channel of an MR imaging machine. The method further comprises exciting precessing nuclear spins in at least a region of the organism adjacent to the at least two coils within the organism. The method also comprises using a partially parallel acquisition technique to simultaneously sample a plurality of response signals with the coils to form a reduced k-space dataset for each of the at least two coils. The response signals represent nuclear magnetic resonance signals arising from the precessing nuclear spins in the region.

Another embodiment of the present invention comprises a system for performing parallel MR imaging. The system includes a magnetic resonance imaging machine including at least two RF receiver channels. The system further includes a probe including at least two MR RF reception coils. Each of the at least two coils is operationally connected to a separate one of the at least two receiver channels. The magnetic resonance imaging machine uses a partially parallel acquisition technique, during an internal imaging procedure on an organism, to simultaneously sample a plurality of magnetic resonance response signals with the coils to form a reduced k-space dataset for each of the at least two coils such that a resultant acquisition acceleration is along a phase-encoded direction which is parallel to an axial direction through the at least two MR RF reception coils within the probe.

A further embodiment of the present invention provides a method to perform intravascular, three-dimensional MR imaging. The method comprises inserting an intravascular catheter into a liquid-carrying vessel (e.g., a blood vessel) of an organism (e.g., a human patient) at a first position. The intravascular catheter includes at least two MR RF reception coils. Each of the coils is operationally connected to a separate receiver channel of an MR imaging machine. The method further comprises using a partially parallel acquisition technique to excite precessing nuclear spins in and around the vessel, and to sample a plurality of response signals with the coils to form reduced k-space datasets for each coil as the catheter is pulled back through the vessel at a rate of at least 2.0 millimeters per second. The plurality of response signals represent nuclear magnetic resonance signals arising from the precessing nuclear spins. The method also includes processing the acquired reduced k-space datasets to generate a 3-D volume dataset over a length of the vessel.

These and other advantages and novel features of the present invention, as well as details of an illustrated embodiment thereof, will be more fully understood from the following description and drawings.

DETAILED DESCRIPTION OF THE INVENTION

Figure 1:
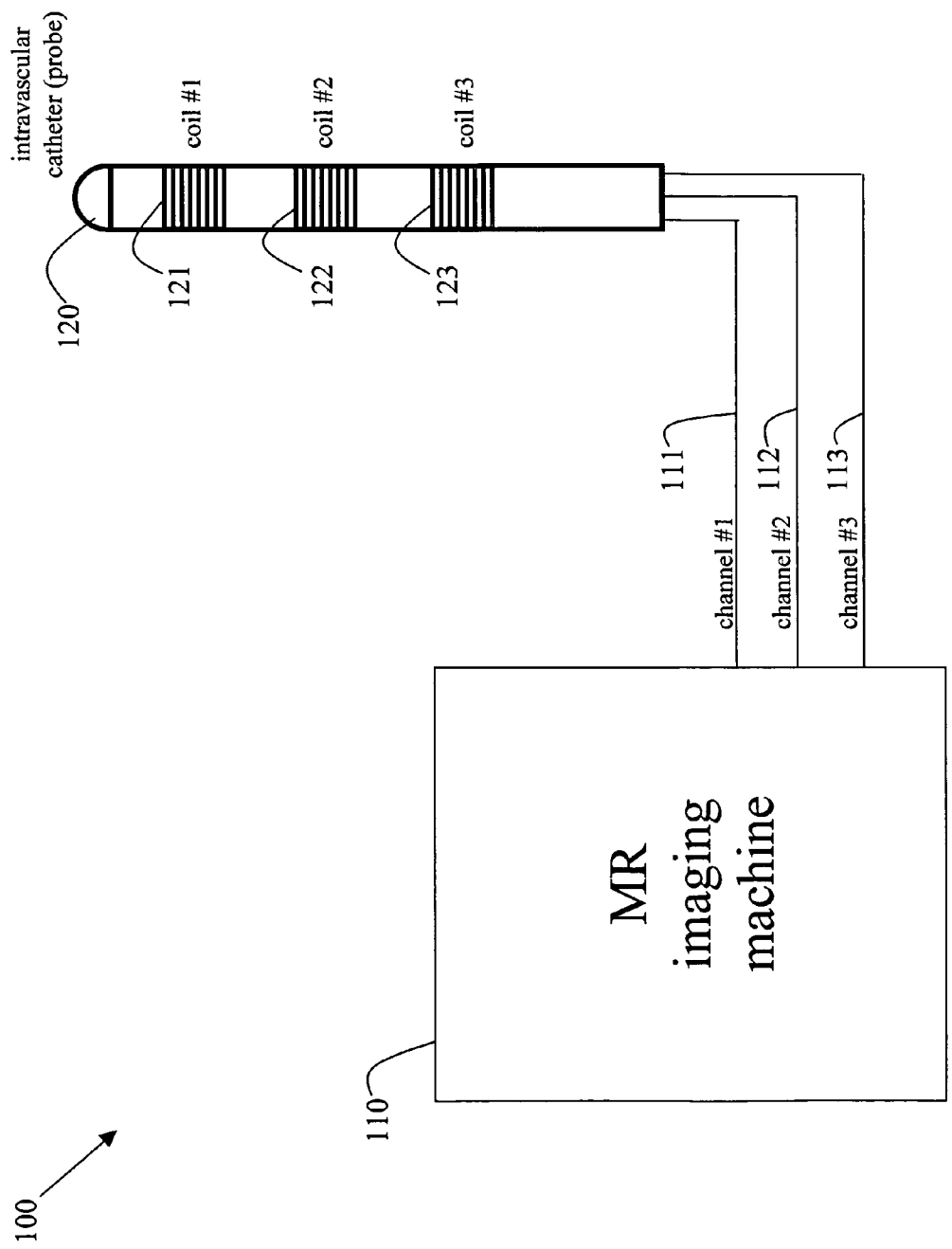
FIG. 1 is a schematic block diagram of an exemplary embodiment of a system for performing parallel MR imaging, in accordance with various aspects of the present invention.

FIG. 1 is a schematic block diagram of an exemplary embodiment of a system 100 for performing parallel MR imaging (e.g., intravascular, three-dimensional MR imaging), in accordance with various aspects of the present invention. The system 100 includes a magnetic resonance (MR) imaging machine 110 and a probe 120 (e.g., an intravascular catheter). The MR imaging machine 110 includes three RF receiver channels 111-113 (channel #1, channel #2, and channel #3). The intravascular catheter 120 includes three MR RF reception coils 121-123 (coil #1, coil #2, and coil #3). Each of the reception coils 121-123 are operationally connected to a separate receiver channel 111-113 of the MR imaging machine. For example, coil #1 121 is connected to channel #1 111, coil #2 122 is connected to channel #2 112, and coil #3 123 is connected to channel #3 113. As a result, the three reception coils 121-123 may be used to simultaneously receive magnetic resonance signals in parallel and propagate the magnetic resonance signals to the MR imaging machine via the three RF receiver channels 111-113.

As used herein, the term "probe" may refer to any of various types of catheters and probes that may be used for internal imaging of an organism (e.g., a human patient). For example, the probe may be an endo-rectal probe for internally imaging a prostate gland of a patient or may be part of a biopsy needle. Also, as used herein, the phrase "internal imaging" means that the MR RF reception coils used for imaging are inserted inside of the patient or organism as part of a probe. A coil may take the form of a spiral solenoid, a single loop, a rectangular multi-loop coil, as well as other configurations or combinations of configurations that allow parallel imaging along the long axial direction of the probe, in accordance with various aspects of the present invention.

In accordance with an embodiment of the present invention, the MR imaging machine 100 may include various standard components and subsystems (not shown in FIG. 1) such as, for example, a field magnet, shim coils, a shim power supply, gradient coils, amplifiers, digital-to-analog converters, a sequence controller, RF transmission coils, an RF subsystem, a system computer, a transmission/reception diplexer, an RF amplifier, analog-to-digital converters, an image computer, a synthesizer, and a user interface. See U.S. Pat. No. 6,841,998, which is incorporated herein by reference, for more details on these standard components and subsystems and how they interact with each other. For simplicity and for the purpose of focusing on embodiments of the present invention, the MR imaging machine 100 is shown in FIG. 1 as a simple block with the three receiver channels 111-113 interfacing to the three reception coils 121-123 in an intravascular catheter 120.

Figure 2:
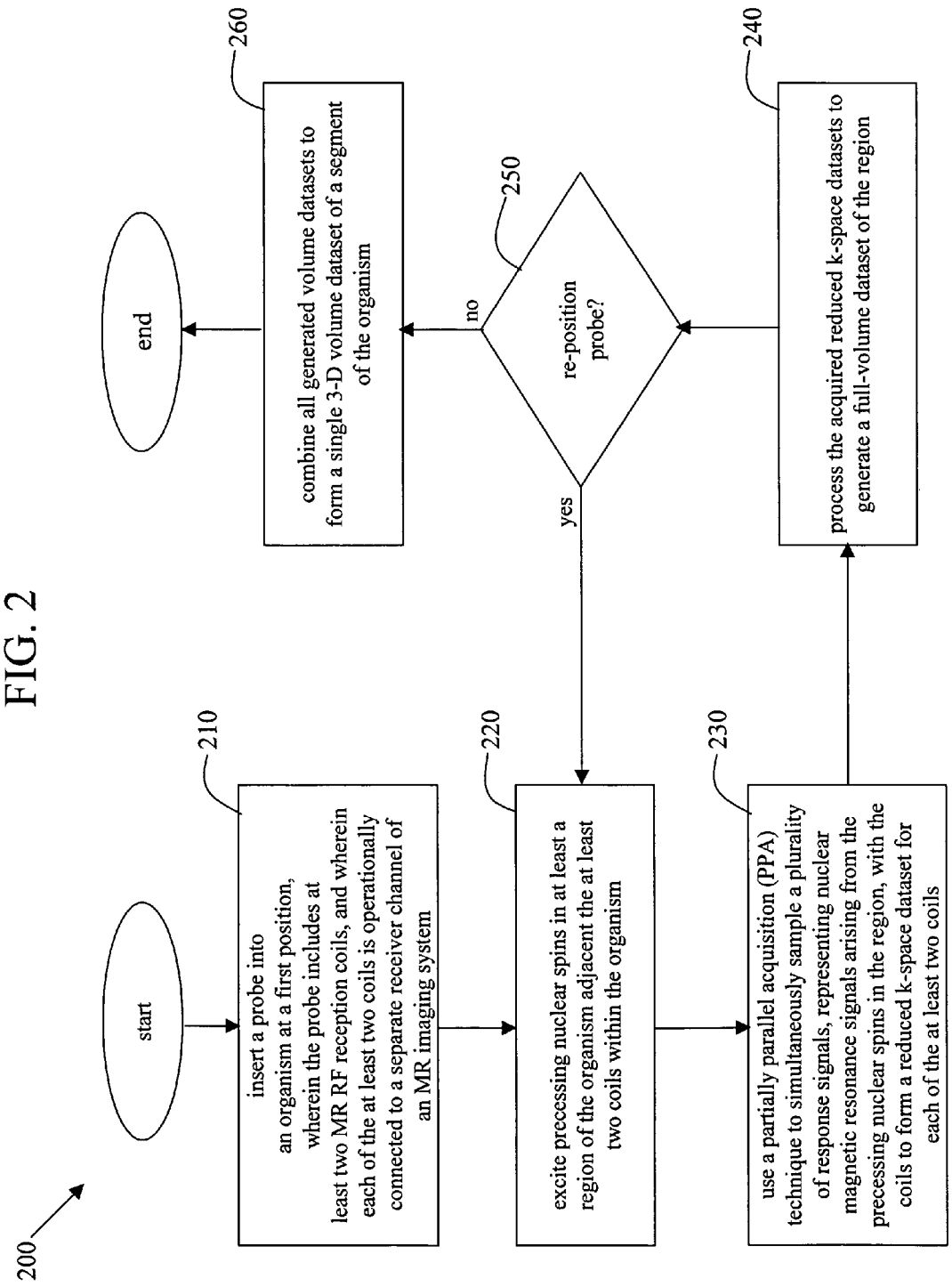
FIG. 2 is a flowchart of a first exemplary embodiment of a method to perform parallel MR imaging using the system of FIG. 1, in accordance with various aspects of the present invention.

FIG. 2 is a flowchart of a first exemplary embodiment of a method 200 to perform parallel MR imaging using the system 100 of FIG. 1, in accordance with various aspects of the present invention. In step 210, a probe is inserted into an organism at a first position, wherein the probe includes at least two MR RF reception coils, and wherein each of the at least two coils is operationally connected to a separate receiver channel of an MR imaging machine. In step 220, precessing nuclear spins are excited in at least a region of the organism adjacent the at least two coils within the organism. For example, certain components and subsystems of the MR imaging machine 100 are used to excite the nuclear spins (e.g., field magnet, gradient coils, etc.). In step 230, a partially parallel acquisition (PPA) technique is used to simultaneously sample a plurality of response signals, representing nuclear magnetic resonance signals arising from the precessing nuclear spins in the region, with the coils to form a reduced k-space dataset for each of the at least two coils. In step 240, the acquired reduced k-space datasets are processed to generate a full-volume dataset of the region. As defined herein, a full-volume dataset is a dataset that is not under-sampled (i.e., is not a reduced dataset). In step 250, a decision is made to re-position the probe or not for continued imaging. If the probe is re-positioned then, the method reverts back to steps 220-240 to generate another full-volume dataset of a new region corresponding to the re-positioned probe. The re-positioning of the probe may be repeated a plurality of times to gather data over a segment of the organism (e.g., over a length segment of a blood vessel). Then, in step 260, all of the generated full-volume datasets are combined to form a single 3-D volume dataset of the segment of the organism.

The general idea herein is to use a partially parallel acquisition technique to reduce the acquisition time for internal MR imaging, and yet, be able to reconstruct a full-volume dataset from the reduced k-space data sets received by each coil. This is accomplished by performing phase encoding in a direction along the length of the probe such that the coils within the probe are spaced along the phase encoding direction. During the excitation and sampling process, the signals are under-sampled along the phase encoding direction and the spatial separation of the multiple coils along the phase encoding direction allows for the under-sampled data from each coil to be used to generate a full-volume dataset for the sampled region, as if no under-sampling was done.

However, under-sampling is done and results in reduced acquisition times. Each MR RF reception coil samples a reduced k-space dataset in parallel (i.e., at the same time) with each of the other MR RF reception coils. In other words, spatial information contained in the component coils of the catheter is used to partially replace spatial encoding which would normally be performed using gradients. The resultant full-volume dataset may comprise a complete k-space dataset or a complete spatially transformed image dataset.

Various partial parallel acquisition (PPA) techniques may be used to form, for example, intravascular images, in accordance with various embodiments of the present invention. Some examples of PPA techniques include GRAPPA (Generalized Auto-Calibrating Partially Parallel Acquisition) and SMASH (Simultaneous Acquisition of Spatial Harmonics), which are performed in the Fourier or k-space domain, and SENSE (Sensitivity Encoding) which is performed in the image domain. Other PPA techniques are possible as well, in accordance with other embodiments of the present invention. Certain PPA techniques sample additional auto-calibration signal (ACS) lines for the purpose of accounting for non-uniformity in the sensitivity profiles of the reception coils. The ACS technique is part of the overall PPA technique.

In accordance with an embodiment of the present invention, mixed datasets may be acquired over several catheter positions. For example, at a first catheter position, reduced datasets may be acquired. At a second catheter position, full datasets may be acquired. And at a third catheter position, reduced datasets may again be acquired for each coil. Therefore, in accordance with an embodiment of the present invention, such mixed datasets may be acquired. Any 3-D volume along the length of a vessel may be formed using several different types of acquisition (e.g., PPA or full-parallel).

Also, different sequences may be used at the different catheter positions to obtain certain contrast effects. For example, a first dataset at a first catheter position may be acquired using a T1-weighted sequence. A second dataset at a second catheter position may be acquired using a T2-weighted sequence. Any combination of full or reduced datasets with various types of sequences are possible, in accordance with various embodiments of the present invention.

Figure 3:
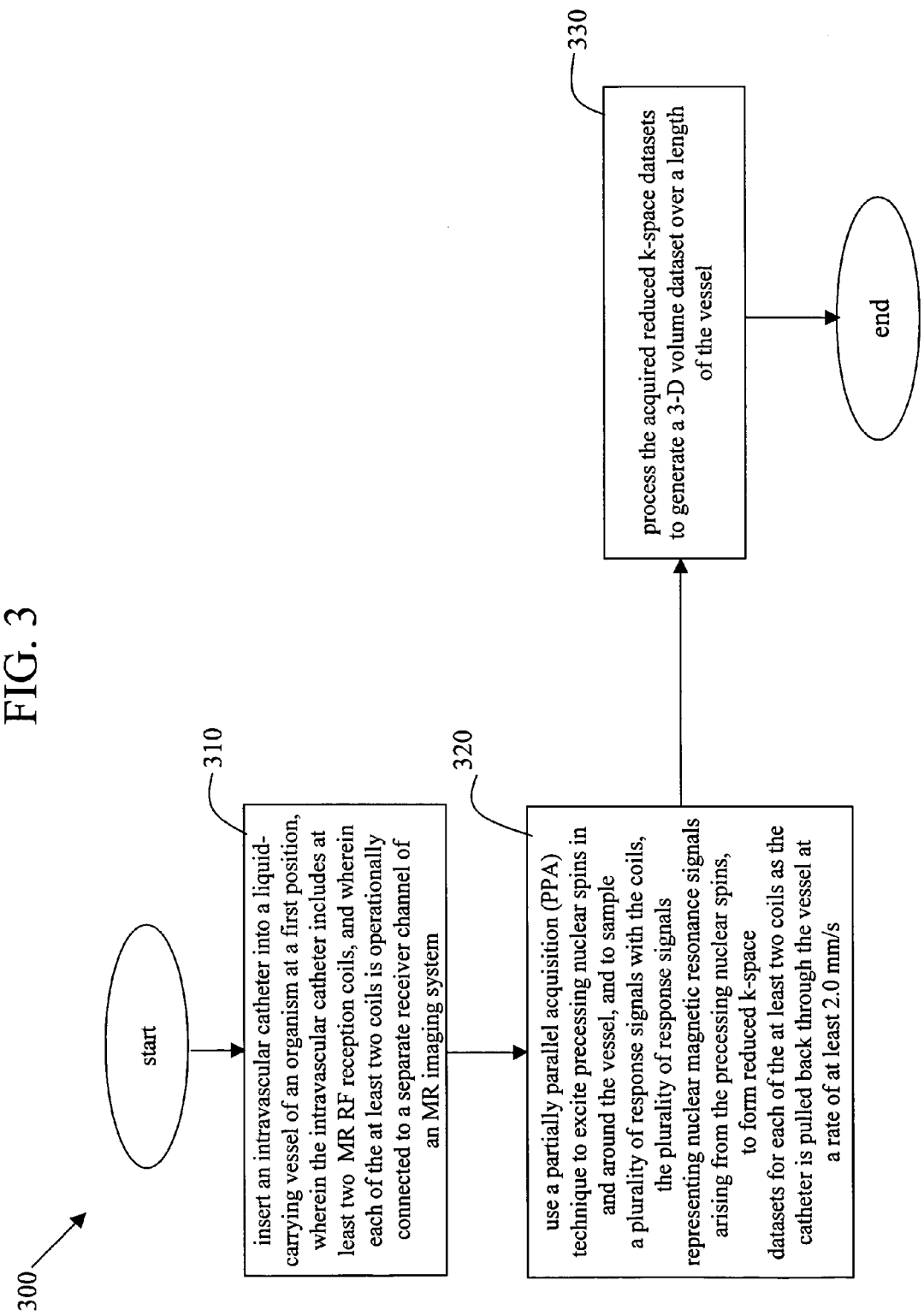
FIG. 3 is a flowchart of a second exemplary embodiment of a method to perform parallel MR imaging using the system of FIG. 1, in accordance with various aspects of the present invention.

FIG. 3 is a flowchart of a second exemplary embodiment of a method 300 to perform intravascular, three-dimensional MR imaging using the system 100 of FIG. 1, in accordance with various aspects of the present invention. In step 310, an intravascular catheter is inserted into a liquid-carrying vessel of an organism at a first position. The intravascular catheter includes at least two MR RF reception coils and each of the two coils is operationally connected to a separate receiver channel of an MR imaging machine. In step 320, a partially parallel acquisition (PPA) technique is used to excite precessing nuclear spins in and around the vessel, and to sample a plurality of response signals with the coils, the plurality of response signals representing nuclear magnetic resonance signals arising from the precessing nuclear spins, to form reduced k-space datasets for each of the at least two coils as the catheter is pulled back through the vessel at a rate of at least 2.0 mm per second. In step 330, the acquired reduced k-space datasets are processed to generate a 3-D volume dataset over a length of the vessel. Again, any number of PPA techniques may be employed in the method 300, in accordance with various embodiments of the present invention. The catheter may be pulled back automatically using, for example, an automatic pull-back device that is connected to the catheter. The automatic pull-back device can be set by a user to provide an effective pull-back speed of the catheter for acquisition over a length segment of a vessel. Other pull-back speeds, which may be greater than or less than 2.0 mm per second, are possible as well, in accordance with various aspects of the present invention.

Figure 4:
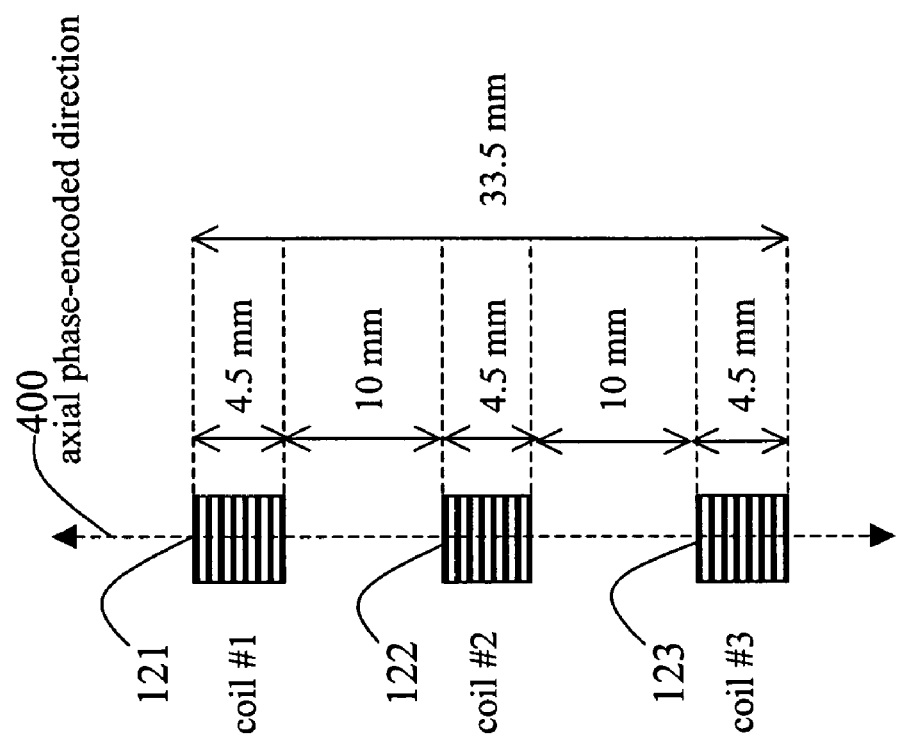
FIG. 4 illustrates an exemplary embodiment of three coils spaced within the catheter of FIG. 1, in accordance with various aspects of the present invention.

FIG. 4 illustrates an exemplary embodiment of three coils 121-123 spaced within the catheter 120 of FIG. 1, in accordance with various aspects of the present invention. In accordance with an embodiment of the present invention, the coils 121-123 may be opposed solenoid coils wound from 30 AWG copper magnet wire. Each coil may be 5 F in diameter, have 5 windings per coil, and have a length of 4.5 mm. The spacing between the coils may be 10 mm. The overall length of the coil configuration is 33.5 mm. With the coils 121-123 positioned within the catheter 120, tuning, matching and passive decoupling are performed near the tip of the catheter 120. The resultant maximum outer diameter of the catheter 120 is 11 F. Again, the coils 121-123 are linearly arranged along a phase encoded direction 400 which is parallel to the long axis of the coil/catheter (i.e., perpendicular to the radial axis).

Figure 5A:
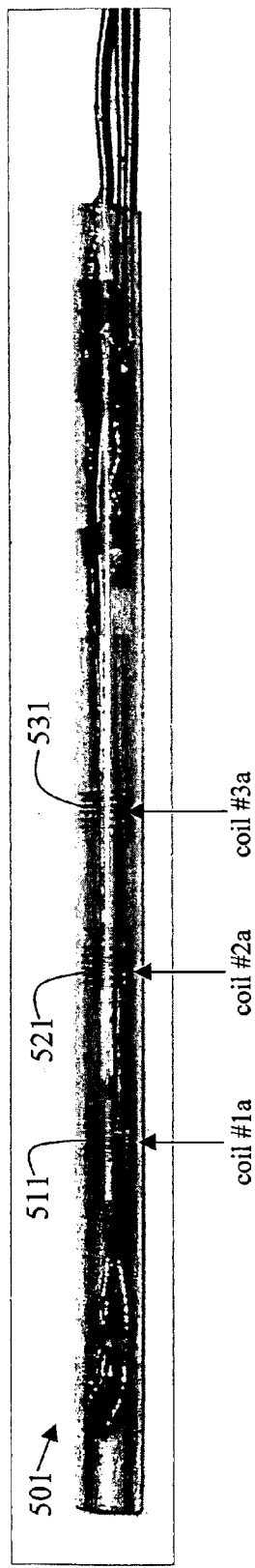
FIG. 5a illustrates an exemplary embodiment of an intravascular catheter having three coils, in accordance with various aspects of the present invention.

As a further example, FIG. 5a illustrates an exemplary embodiment of an intravascular catheter 501 having three coils 511, 521, and 531, in accordance with various aspects of the present invention. Each coil may be operationally connected (e.g., via conductive wiring) to a separate receiver channel of an MR imaging machine in order to perform intravascular partial parallel acquisition (PPA) to image, for example, blood vessels within a human patient.

Figure 5B:
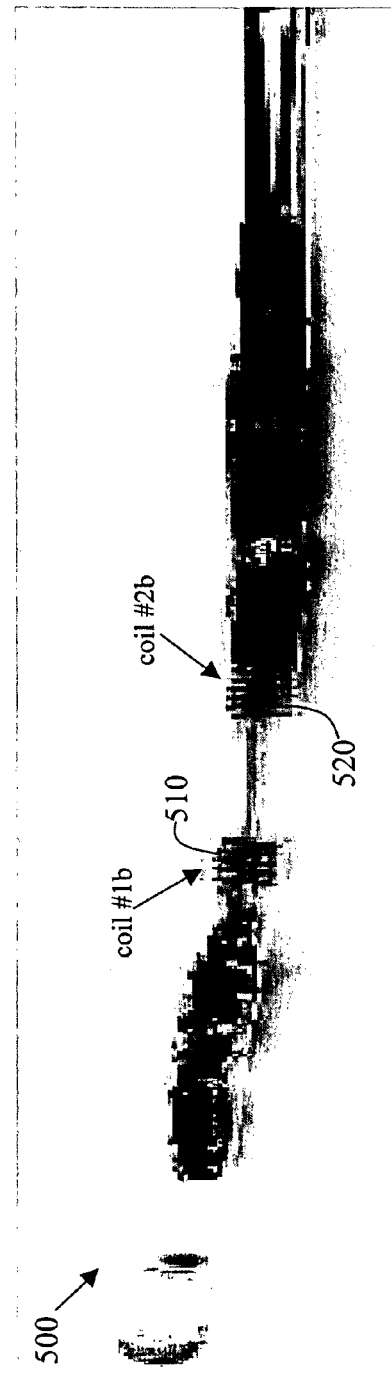
FIG. 5b illustrates an exemplary embodiment of an intravascular catheter having only two coils, in accordance with various aspects of the present invention.

FIG. 5b illustrates an exemplary embodiment of an intravascular catheter 500 having only two coils 510 and 520, in accordance with various aspects of the present invention. Again, each of the two coils may be operationally connected (e.g., via conductive wiring) to a separate receiver channel of an MR imaging machine in order to perform intravascular partial parallel acquisition (PPA) to image, for example, blood vessels within a human patient.

When multiple full-volume datasets are generated, each at a different catheter position along a segment of a vessel, the full-volume datasets may be combined to form a single 3-D dataset. The individual full-volume datasets may correspond to vessel regions which are directly adjacent to each other, or which may overlap each other. Once a full-volume 3-D dataset is generated, an image slice may be formed along any arbitrary image plane through the full-volume dataset. In accordance with an embodiment of the present invention, a single full-volume data set may already correspond to a 2-D slice through the organism being internally imaged.

Figure 6:
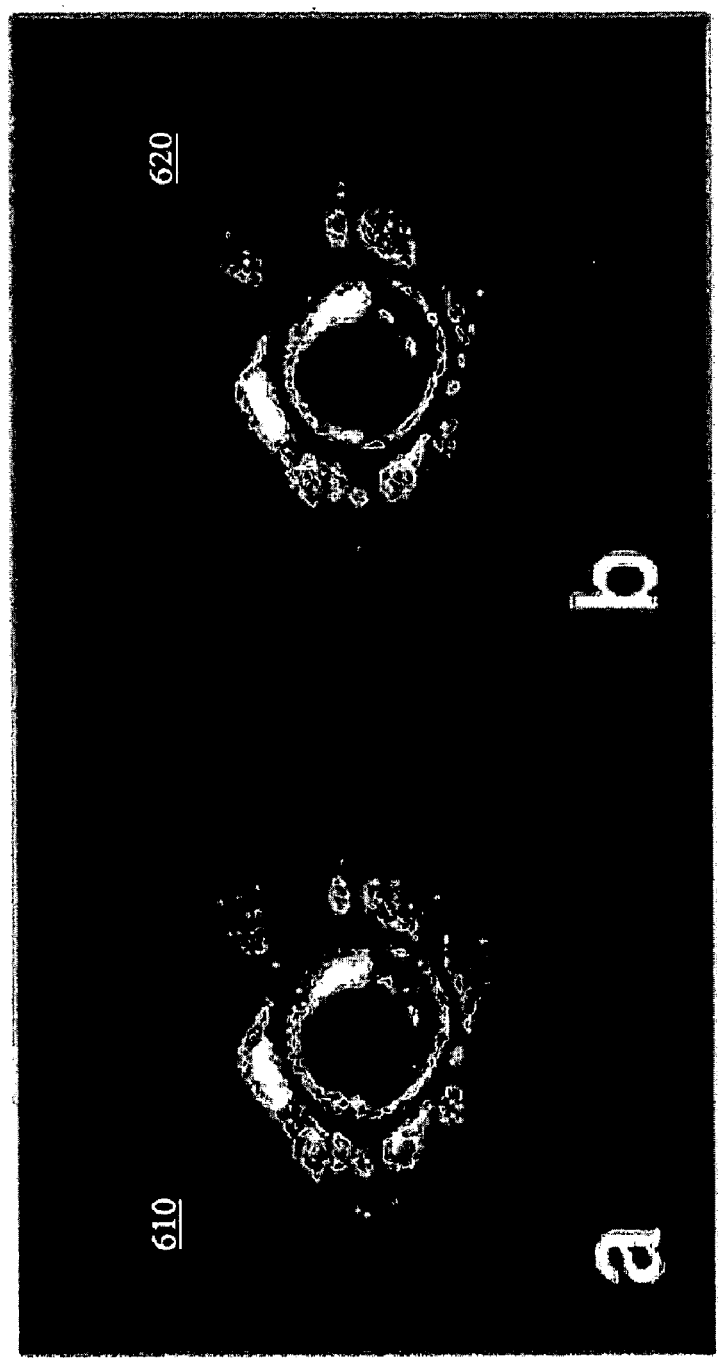
FIG. 6a illustrates an exemplary image of a first vascular region formed using the system of FIG. 1 and the method of FIG. 2, in accordance with an embodiment of the present invention.
FIG. 6b illustrates an exemplary image of the first vascular region of FIG. 6a formed using a slower, conventional acquisition method.

FIG. 6a illustrates an exemplary image 610 of a first vascular region formed using the system 100 (e.g., a Siemens Magnetom Sonata 1.5T whole body scanner) of FIG. 1 and the method 200 of FIG. 2, in accordance with an embodiment of the present invention. Image 610 is an in situ image of an accelerated (R=2) 3D-TrueFISP dataset from the abdominal aorta in a pig. The imaging parameters are: TE/TR 6.6/13.2 ms, α=55°, matrix 128×128, FOV 30 mm, 32 slices, SL 2 mm (64 m partition thickness), and TA=27 seconds for the partially parallel acquisition (i.e., an acceleration factor of 2, a.k.a. a reduction factor of R=2).

FIG. 6b illustrates an exemplary image 620 of the first vascular region of FIG. 6a formed using a slower, conventional acquisition method. Image 620 is an in situ image of an accelerated (R=2) 3D-TrueFISP dataset from the abdominal aorta in a pig. The imaging parameters are: TE/TR 6.6/13.2 ms, α=55°, matrix 128×128, FOV 30 mm, 32 slices, SL 2 mm (64 m partition thickness), and TA=54 seconds for the full data acquisition.

Comparison of images 610 and 620 reveal essentially equivalent overall image quality for both standard and PPA acquisitions, as well as clear delineation of the vessel wall and surrounding tissue structures in both cases. Compromising artifacts from the PPA reconstruction are not observed. Decreased signal-to-noise ratio (SNR) is apparent in the PPA image 610 outside the region of interest where the coil sensitivity is lowest. However, SNR differences are less than 41.4% as predicted by the decreased acquisition time and use of parallel imaging, suggesting a successful trade-off in acquisition time and motion artifact immunity. Higher acceleration factors (e.g., 3 and 4 or more) are possible as well, in accordance with various embodiments of the present invention. Different sequence types such as, for example, gradient echo sequences, SSFP sequences, and spin-echo sequences may be used, in accordance with various embodiments of the present invention. Higher pull-back speeds may be achieved using more coil elements and approaching higher acceleration factors.

Figure 7:
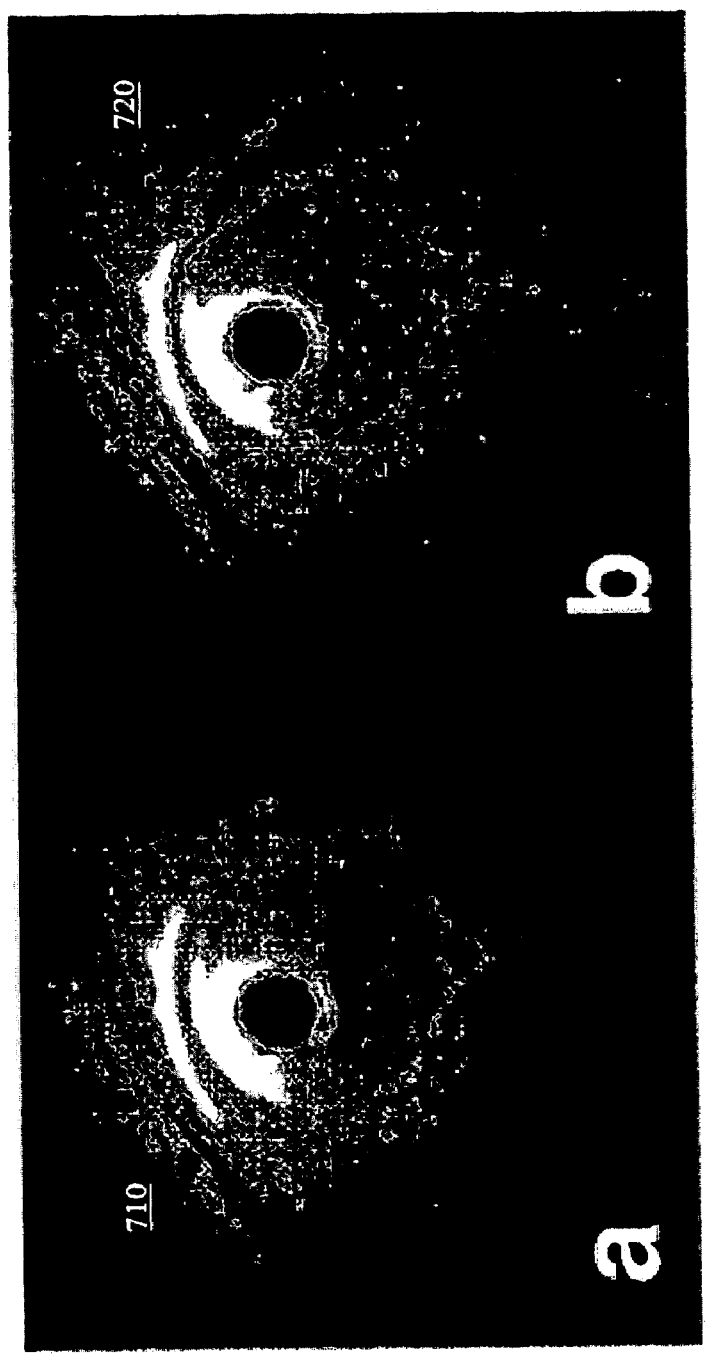
FIG. 7a illustrates an exemplary image of a second vascular region formed using the system of FIG. 1 and the method of FIG. 2, in accordance with an embodiment of the present invention.
FIG. 7b illustrates an exemplary image of the second vascular region of FIG. 7a formed using a slower, conventional acquisition method.

FIG. 7a illustrates an exemplary image 710 of a second vascular region formed using the system 100 of FIG. 1 and the method 200 of FIG. 2, in accordance with an embodiment of the present invention. Image 710 is an in vivo dataset acquired using a 3D FLASH sequence, where saturation pulses are applied to suppress arterial flow. The imaging parameters are:

TE/TR 22/57 ms, α=55°, matrix 128×128, FOV 58 mm, 30 slices, SL 2 mm, TA=42 seconds for the dataset accelerated by a factor of two (i.e., partially parallel acquisition).

FIG. 7b illustrates an exemplary image 720 of the second vascular region of FIG. 7a formed using a slower, conventional acquisition method. Image 720 is an in vivo dataset acquired using a 3D FLASH sequence, where saturation pulses are applied to suppress arterial flow. The imaging parameters are: TE/TR 22/57 ms, α=55°, matrix 128×128, FOV 58 mm, 30 slices, SL 2 mm, TA=84 seconds for the full dataset (i.e., no acceleration). Again, partial parallel imaging (FIG. 7a) showed very good performance at half the measurement time required by standard imaging (FIG. 7b).

In summary, using partially parallel MR acquisition techniques in combination with internal (e.g., intravascular) imaging, using at least two MR RF reception coils within a probe and operationally connected to different RF receiver channels of an MR imaging machine, allows for significantly reduced acquisition times while maintaining good image quality and artifact immunity. The reduced acquisition times and good image quality show that intravascular 3-D parallel imaging can compete with intravascular ultrasound (IVUS). Long vessel segments may be acquired in high resolution by the use of a catheter-based array of coils and using 3-D parallel imaging. Cross-sectional images with a radially symmetrical sensitivity profile and an in-plane resolution comparable to IVUS datasets may be achieved.

The methods, techniques, and systems described herein are not limited to intravascular imaging and fluid carrying vessels, and may be applied to other types of internal imaging as well. For example, a multi-coil catheter may be configured as an endo-rectal probe for prostate examination. Other types of internal imaging, using the basic principles described herein, are possible as well such as asaphogeal imaging, urinary track imaging, etc. In general, the methods, techniques, and systems described herein may be used for imaging any internal parts of the body that may be properly accessed by a catheter or probe.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method of controlling a magnetic resonance (MR) apparatus, where a probe, located in a vasculature of an organism at a first position, includes at least two magnetic resonance (MR) radio frequency (RF) reception coils, where the at least two MR RF reception coils are arranged linearly in the axial direction of the probe, and where the at least two MR RF reception coils are operationally connected to separate receiver channels of an MR imaging system that includes the MR apparatus, the method comprising:

controlling the MR apparatus to create a single $B_0$ field;

controlling the MR apparatus to excite, using a first MR pulse sequence, first precessing nuclear spins in at least a first region of the organism adjacent to the at least two MR RF reception coils in the organism, where the first MR pulse sequence is configured to phase encode the first precessing nuclear spins in a direction parallel to the axial direction of the probe, and where the first precessing nuclear spins are in the $B_0$ field;

receiving a first plurality of response signals in the at least two MR RF reception coils, the first plurality of response signals representing nuclear magnetic resonance (NMR) signals from the first precessing spins in the first region;

controlling the MR apparatus to simultaneously sample the first plurality of response signals using a first partially parallel technique to form a first reduced k-space dataset for each of the at least two MR RF reception coils; and processing the acquired first reduced k-space dataset for each of the at least two MR RF reception coils to generate a first full-volume dataset of the first region, where processing the first reduced k-space data set for each of the at least two MR RF reception coils is based, at least in part, on spatial information associated with the relative positions of the at least two MR RF reception coils.

2. The method of claim 1, where the at least two MR RF reception coils comprise solenoids.

3. The method of claim 1, where the first full-volume dataset of the first region comprises a complete k-space dataset of the first region.

4. The method of claim 1, where the first full-volume dataset of the first region comprises a spatially transformed image dataset of the first region.

5. The method of claim 1, comprising forming an image slice along a selected image plane through the first full-volume dataset of the first region.

6. The method of claim 1, where the first full-volume dataset corresponds to a 2-D slice through the organism.

7. The method of claim 1, comprising:

repositioning the probe in the vasculature of the organism;

controlling the MR apparatus to maintain the single $B_0$ field;

controlling the MR apparatus to excite, using a second MR pulse sequence, second precessing nuclear spins in at least a second region of the organism adjacent to the at least two coils within the organism, where the second MR pulse sequence is configured to phase encode the second precessing nuclear spins in a direction parallel to the axial direction of the probe, and where the second precessing nuclear spins are in the $B_0$ field;

receiving a second plurality of response signals in the at least two MR RF reception coils, the second plurality of response signals representing NMR signals from the second precessing spins in the second region;

controlling the MR apparatus to use a second partially parallel acquisition technique to simultaneously sample the second plurality of response signals to form a second reduced k-space dataset for each of the at least MR RF reception two coils; and processing the acquired second reduced k-space dataset for each of the at least two MR RF reception coils to generate a second full-volume dataset of the second region, where processing the second reduced k-space dataset for each of the at least two MR RF reception coils is based, at least in part, on spatial information associated with the relative positions of the at least two MR RF reception coils.

8. The method of claim 7, comprising processing the first full-volume dataset and the second full-volume dataset to form a single 3-D volume dataset of the first region and the second regions.

9. The method of claim 7, where the second region partially overlaps the first region.

10. The method of claim 7, where the second region is adjacent to the first region and does not overlap the first region.

11. The method of claim 7, where the first MR pulse sequence is different than the second MR pulse sequence.

12. The method of claim 7, where the first partially parallel technique is different than the second partially parallel technique.

13. The method of claim 12 where repositioning the probe comprises automatically pulling the probe through the organism at an effective, predetermined pull-back speed.

14. The method of claim 13 where the effective, predetermined pull-back speed exceeds 2.5 millimeters per second.

15. The method of claim 1, comprising:
   repositioning the probe in the vasculature of the organism;
   controlling the MR apparatus to maintain the single $B_0$ field;
   controlling the MR apparatus to excite, using a second MR pulse sequence, second precessing nuclear spins in at least a second region of the organism adjacent to the at least two coils within the organism, where the second MR pulse sequence is configured to phase encode the second precessing nuclear spins in a direction parallel to the axial direction of the probe, and where the second precessing nuclear spins are in the $B_0$ field;
   receiving a second plurality of response signals in the at least two MR RF reception coils, the second plurality of response signals representing NMR signals from the second precessing spins in the second region; and
   controlling the MR apparatus to acquire a full dataset from the repositioned probe.

* * * * *

UNITED STATES PATENT AND TRADEMARK OFFICE
CERTIFICATE OF CORRECTION

PATENT NO. : 7,606,612 B2
APPLICATION NO. : 11/132989
DATED : October 20, 2009
INVENTOR(S) : Hillenbrand et al.

Page 1 of 1

It is certified that error appears in the above-identified patent and that said Letters Patent is hereby corrected as shown below:

Claims:

In column 8, lines 49-50, delete "at least MR RF reception two coils" and insert --at least two MR RF reception coils--.

In column 8, line 62, delete "regions" and insert --region--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,606,612 B2 |
| APPLICATION NO. | : 11/132989 |
| DATED | : October 20, 2009 |
| INVENTOR(S) | : Hillenbrand et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 589 days.

Signed and Sealed this

Twelfth Day of October, 2010

David J. Kappos
*Director of the United States Patent and Trademark Office*